(12) United States Patent
Schütz et al.

(10) Patent No.: US 6,973,694 B2
(45) Date of Patent: Dec. 13, 2005

(54) ELECTRIC TOOTHBRUSH

(75) Inventors: Alfred Schütz, Zollikofen (CH); Andrea Ragazzo, Bern (CH)

(73) Assignee: Gimelli Produktions AG, Zollikofen (CH)

( * ) Notice: Subject to any disclaimer, the term of this patent is extended or adjusted under 35 U.S.C. 154(b) by 73 days.

(21) Appl. No.: 10/403,504

(22) Filed: Apr. 1, 2003

(65) Prior Publication Data

US 2003/0213076 A1   Nov. 20, 2003

(30) Foreign Application Priority Data

Apr. 4, 2002  (DE) ................. 102 14 803

(51) Int. Cl.[7] ............... A61C 17/22; A46B 13/00
(52) U.S. Cl. ......................... 15/22.1; 15/28
(58) Field of Search ................. 15/22.1, 22.4, 15/28, 29, 27, 4

(56) References Cited

U.S. PATENT DOCUMENTS

| | | | |
|---|---|---|---|
| 4,710,995 A | 12/1987 | Joyashiki et al. | |
| 4,989,287 A | 2/1991 | Scherer | |
| 5,068,939 A * | 12/1991 | Holland | 15/22.1 |
| 5,226,206 A * | 7/1993 | Davidovitz et al. | 15/22.1 |
| 5,435,032 A | 7/1995 | McDougall | |
| 5,465,444 A * | 11/1995 | Bigler et al. | 15/22.1 |
| 5,524,312 A | 6/1996 | Tan et al. | |
| 6,148,462 A * | 11/2000 | Zseng | 15/22.1 |
| 2004/0143917 A1 * | 7/2004 | Ek | 15/22.1 |

FOREIGN PATENT DOCUMENTS

| | | |
|---|---|---|
| DE | 4225548 | 2/1994 |
| DE | 29618755 | 3/1997 |
| DE | 19543958 | 5/1997 |
| DE | 19937281 | 2/2001 |
| DE | 19954294 | 5/2001 |
| EP | 0818977 | 10/1999 |
| WO | 96/10373 A1 | 4/1996 |
| WO | 01/06946 A1 | 2/2001 |
| WO | 01/43586 | 6/2001 |

* cited by examiner

*Primary Examiner*—Robert J. Warden, Sr.
*Assistant Examiner*—Shay L. Balsis
(74) *Attorney, Agent, or Firm*—Crowell & Moring LLP

(57) ABSTRACT

An electric toothbrush with a handle and a brush member having a brush head, individual cylindrical bristle holders with tufts of bristles held rotatably in the brush head. They are set into an oscillatory rotating movement by means of a connecting rod executing a reciprocating sliding movement and simultaneously an oscillatory movement about its longitudinal axis, with transverse grooves, disposed therein. In addition, a bristle holder plate in the brush head is held so as to oscillate about a shaft running in the longitudinal direction of the toothbrush. Thus, during the oscillatory movement of the bristle holders the bristle holder plate swivels back and forth in synchronism with the connecting rod.

12 Claims, 8 Drawing Sheets

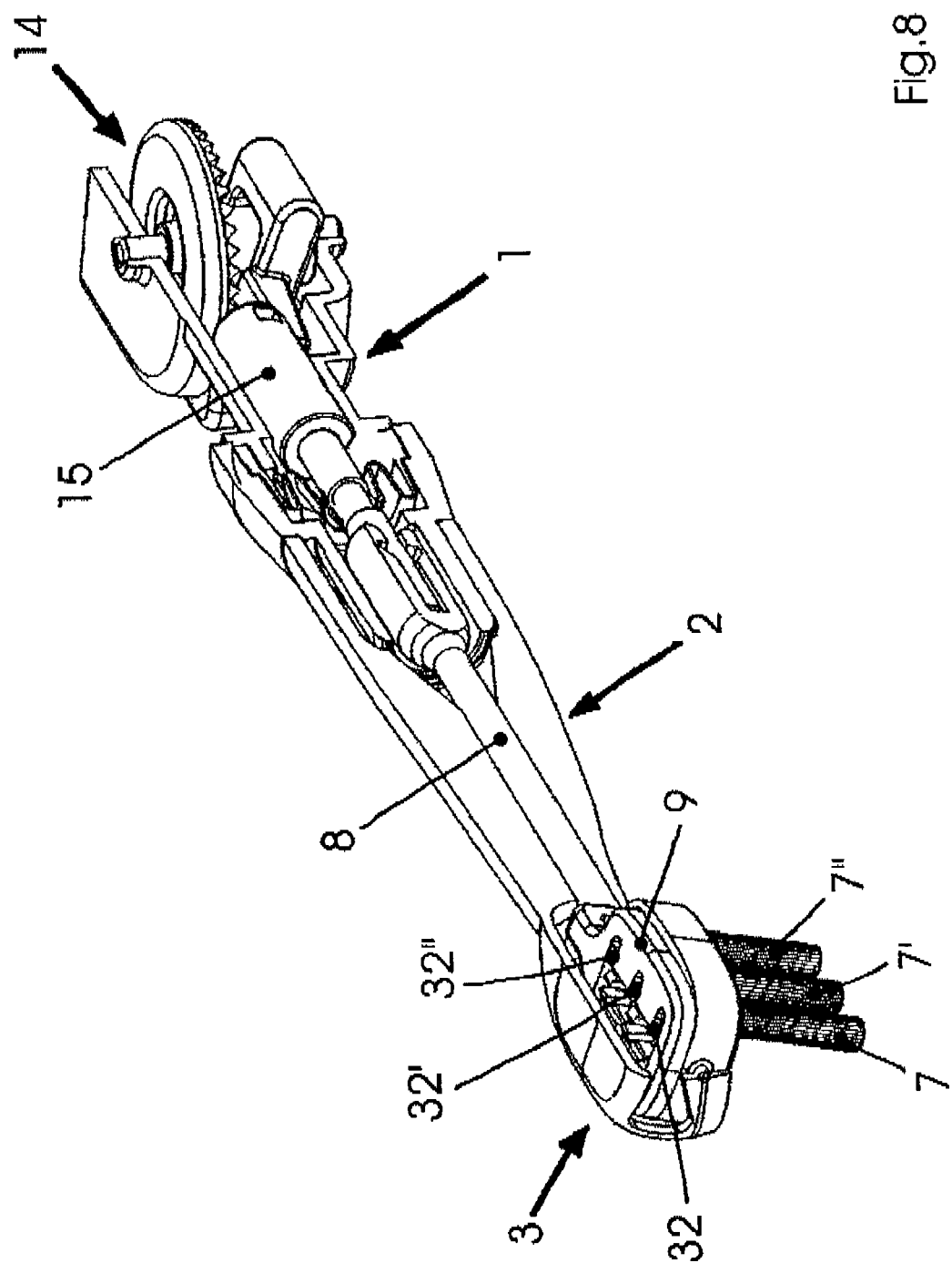

ELECTRIC TOOTHBRUSH

BACKGROUND AND SUMMARY OF THE INVENTION

This invention relates to an electric toothbrush with a handle and a brush member. The brush member has a brush head and a connecting rod which can be set by means of a gear into a sliding movement reciprocating longitudinally. In the electric toothbrush the bristle holders are held rotatably in the brush head in a bristle holder plate. The bristle holders can be set into an oscillatory rotating movement by means of the connecting rod. The brush head can be set into oscillatory movement about the longitudinal axis of the toothbrush by means of the gear.

An electric toothbrush of the above type is the subject matter of U.S. Pat. No. 4,989,287. In the toothbrush, disclosed in this patent, a connecting rod is fixed non-rotatably in the brush member. The brush member is connected rotatably about its longitudinal axis relative to the handle. The gear in the handle produces both the oscillatory movement and the sliding movement. Owing to the oscillatory movement of the connecting rod about its longitudinal axis, the entire brush member oscillates at the same time about its longitudinal axis so that when using the toothbrush, one can hold only the handle and not the comparably large brush member.

In the prior art toothbrush the gear is constructed in such a manner that the design of the two movements that are produced is narrowly defined, because a single eccentric produces both movements and, therefore, a change in its eccentricity, for example for the purpose of enlarging the sliding movement, simultaneously leads to an enlargement of the oscillatory movement.

U.S. Pat. No. 4,710,995 also shows an electric toothbrush, in which one gear is provided for sliding movement and one gear is provided for oscillatory movement, whereby each gear has its own eccentric. Thus, both movements can be dimensioned independently of each other. However, the construction of the toothbrush, according to this patent, is very complicated on the whole because it has a plurality of gears and pinions, a feature, for example, that is illustrated in FIG. 1 of the patent.

EP 0 818 977 also shows an electric toothbrush, wherein the brush member cannot be moved and the brush holder, housed in the toothbrush head, carries out an oscillatory movement. However, this brush holder has stationary bristles and no individual tufts of bristles that can oscillate individually about its longitudinal axis.

The present invention is based on the problem of designing an electric toothbrush of the type described above in such a manner that both an oscillatory movement of the individual bristle holders and an oscillatory swivel movement of the entire unit of bristle holders are possible with simple means, without having to move thereby the entire brush member.

This problem is solved by means of the invention in that the bristle holder plate in the brush head is held so as to oscillate about a shaft running in the longitudinal direction of the toothbrush; and the brush member is connected non-rotatably to the handle, and that the gear for swiveling the bristle holder plate is designed relative to the brush member.

This design makes it possible to non-rotatably connect the brush member to the handle in the conventional manner; and to provide to this end a simple coupling, for example, a bayonet fastener. Thus, the use of the toothbrush is simultaneously more comfortable, because in so doing one can also grasp the handle, because it does not move. Furthermore, the energy consumption of the toothbrush is less than in the conventional toothbrush, because only one relatively small bristle holder plate must be swiveled and not the entire brush member.

It is advantageous if, according to a further aspect of the invention, the gear for producing an oscillatory movement of the connecting rod about its longitudinal axis is formed, and if the connecting rod is held, such that it rotates relative to the brush member about its longitudinal axis, and if the connecting rod rests with its front end so as to slide axially against the bristle holder plate. In such a design the connecting rod is set into motion oscillating about its longitudinal axis. And the motion in the brush head is transferred directly to the bristle holder plate.

The space conditions in the brush head are used optimally if the front end of the connecting rod is bent at right angles and is oriented parallel to the longitudinal axis of the connecting rod.

The electric toothbrush is especially economical to produce if the shaft in the brush head is held on both sides of the bristle holder plate and projects with its free end into the connecting rod that is bent at right angles. Owing to this design, the shaft can swivelably hold not only the bristle holder plate, but also the front area of the connecting rod.

The gear is designed especially simple if it is formed in the handle by means of an eccentric, oriented at right angles to the toothbrush shaft and thus also at right angles to the connecting rod; and a guide member of the toothbrush shaft is formed with a guide, which is oriented at right angles to the longitudinal axis of the toothbrush shaft, and which reaches over the eccentric.

The means for generating the oscillatory movement and the sliding movement are designed especially simple, if, according to another aspect of the invention, the gear is formed exclusively for generating a sliding movement of the toothbrush shaft; and, in addition to the gear, a swivel gear is provided for generating the swiveling movement of the toothbrush shaft.

The swivel gear is economical to manufacture, if it has a twisted flattening on the toothbrush shaft and a radial projection which is stationary in the housing and rests against the flattening.

As an alternative, however, it is possible to provide that the swivel gear has a slanted groove which runs radially into the toothbrush shaft and into which projects a radial projection that is stationary in the housing.

The brush member, which must be replaced from time to time because of wear or contamination and must be on hand over and over again when several persons use the toothbrush, is especially economical to manufacture if the swivel gear is disposed in the handle, just like the gear for the sliding movement.

Another very simple embodiment of the invention resides in the fact that the swivel gear is disposed in the brush head and has a groove, which runs obliquely to the sliding direction of the connecting rod and into which projects an arm, which is oriented radially to the swivel shaft of the bristle holder plate and is connected stationarily to the bristle holder plate. However, it is also possible to provide that the bristle holder plate in the toothbrush head is mounted swivelably on a swivel shaft, which is oriented parallel to the longitudinal axis of the brush member, on two opposing sides; and the connecting rod in the brush member is guided non-rotatably.

When the gear is supposed to produce the sliding movement and the oscillatory movement of the toothbrush shaft, it is especially easy to design if it has a spherical head, designed as an eccentric, and the toothbrush shaft reaches with a ring, offset radially to its longitudinal axis, over this spherical head.

In summary it must be emphasized that the bristle tufts can be pressed or cemented into the respective bristle holder or held in the respective bristle holder through injection molding with plastic. Instead of with eccentric pins and transverse grooves, the reciprocating rotating movement of the bristle holders with the bristle tufts can also be generated in a different way, for example, by means of a gearwheel on each bristle holder and rack teeth on the connecting rod. The holders of the tufts of bristles can be made of material that is different from that of the rest of the toothbrush. On the whole, the inventive toothbrush is designed such that it can be manufactured quite easily from injection molded parts.

Other objects, advantages and novel features of the present invention will become apparent from the following detailed description of the invention when considered in conjunction with the accompanying drawings.

BRIEF DESCRIPTION OF THE DRAWINGS

FIG. 8 is a perspective longitudinal view, partly broken away for illustrative clarity, of the front area of an embodiment of the inventive toothbrush.

DETAILED DESCRIPTION OF THE PREFERRED EMBODIMENTS

Figure 1:
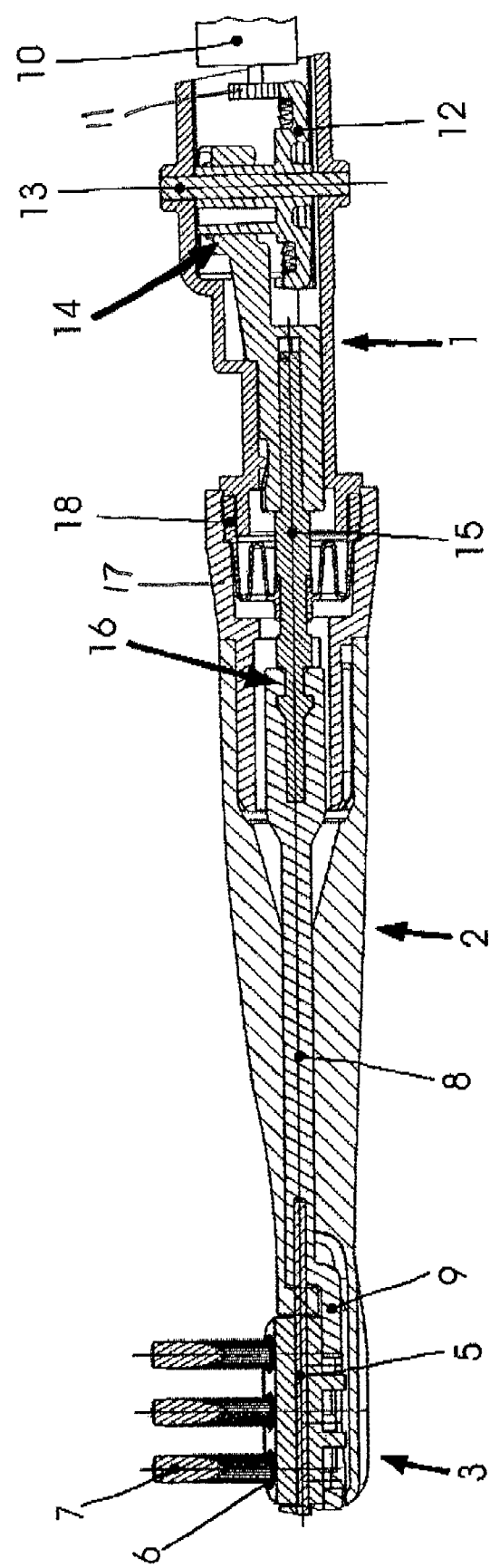
FIG. 1 is a longitudinal view of a toothbrush according to the present invention.
Figure 6:
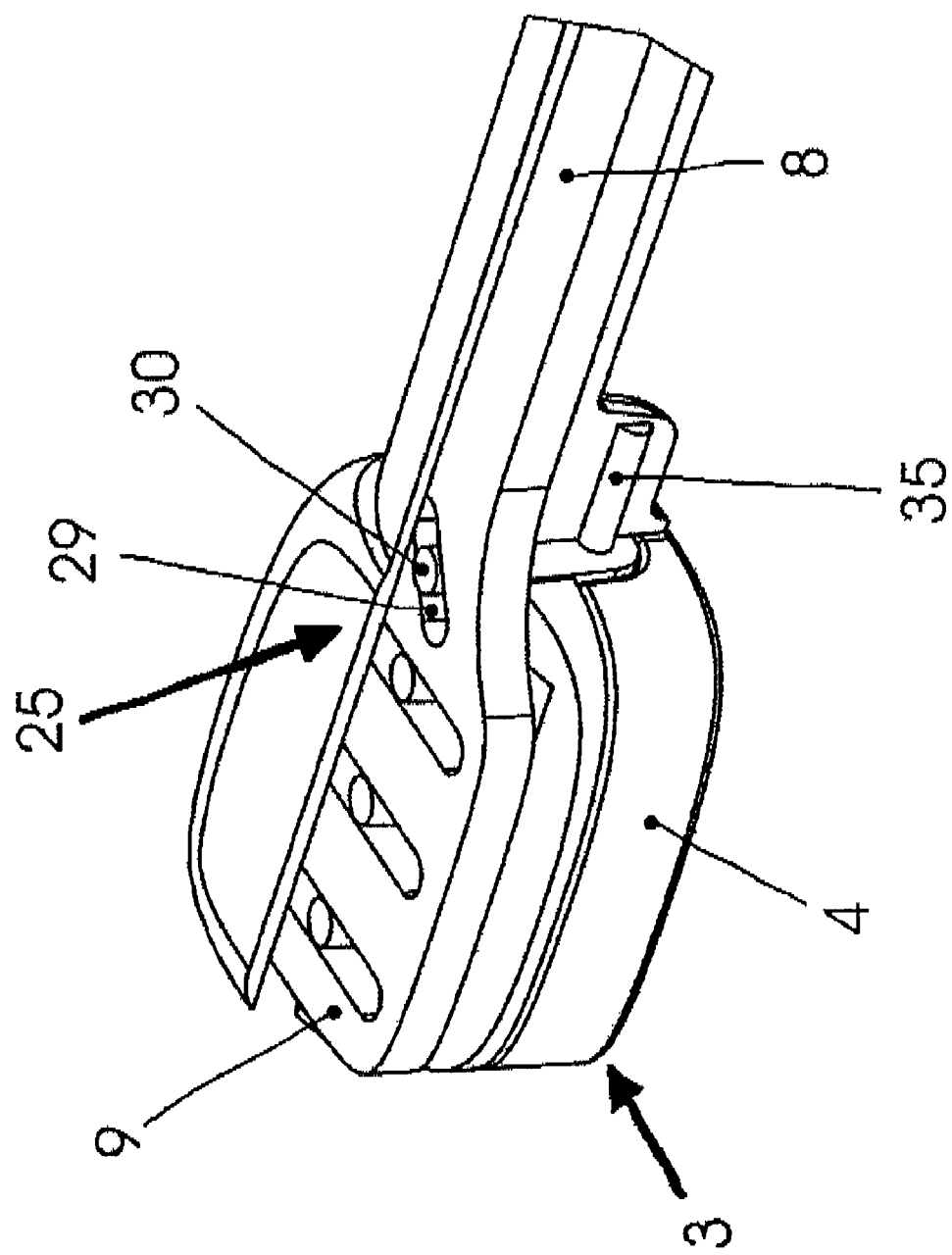
FIG. 6 is a perspective view, partly broken away for illustrative clarity, of a modified embodiment of the toothbrush head.

Referring to FIG. 1, there is shown an electric toothbrush, which has a handle 1 and a brush member 2, designed as a snap on brush. In the front area the brush member 2 forms a brush head 3, which accepts a bristle holder plate 4 (FIG. 6). This bristle holder plate 4 is mounted swivelably on a shaft 5, which is held in the brush head 3 and which runs in the longitudinal direction of the toothbrush.

The bristle holder plate 4 accepts rotatably several cylindrical bristle holders 6 with tufts of bristles 7. Inside the brush member 2 a connecting rod 8 can be slid axially and rotated. This connecting rod 8 has an end 9, which is bent at right angles and which rests against the bristle holder plate 4 and is held swivelably on a free end of the shaft 5. Owing to its oscillatory movement about the longitudinal axis of the connecting rod 8, the offset end 9 can set the bristle holder plate 4 into an oscillatory movement about the shaft 5 and also provides for a reciprocating rotation of the bristle holders 6 with the tufts of bristles 7 owing to the reciprocating sliding movement, oriented in the direction of the longitudinal axis.

The handle 1 has a motor 10, which is shown to some degree and which drives a crown wheel 12 by means of a pinion 11. This crown wheel 12 is mounted rotatably on a crown wheel shaft 13, oriented at right angles to the connecting rod 8. The crown wheel 13 is a part of a gear 14, by means of which a toothbrush shaft 15 of the handle 1 is set into a combined sliding and oscillating movement by means of the revolving rotating movement of the pinion 11. The toothbrush shaft 15 is connected to the connecting rod 8 by means of a disconnectable coupling 16 in such a manner that it carries out the same movement as the toothbrush shaft 15. In addition, it is clear from FIG. 1 that the brush member 2 has a housing 17, which is slid on a housing shoulder 18 of the handle 1, where it is secured axially by means of a bayonet lock, which is not shown.

Figure 2:
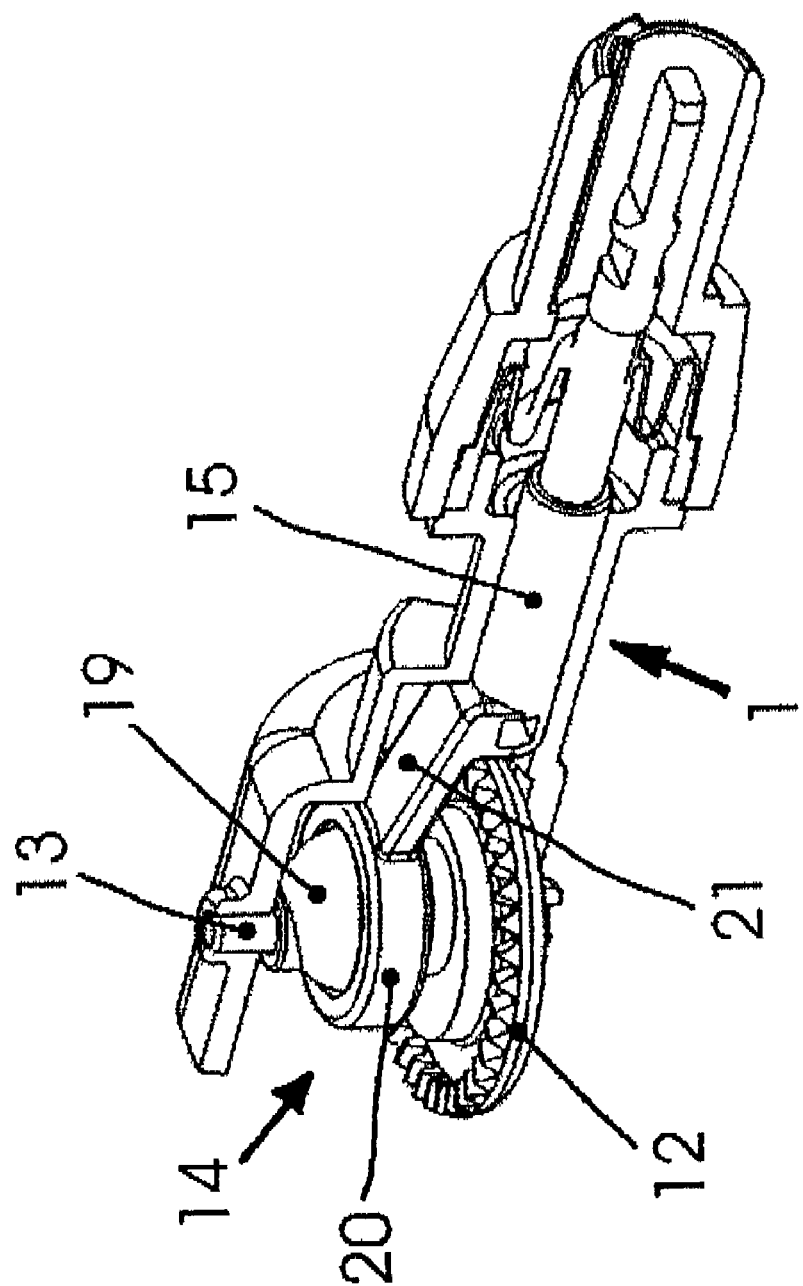
FIG. 2 is a perspective longitudinal view in cross-section of a gear area in the handle of the toothbrush.

FIG. 2 shows a possible embodiment of the gear 14 in the handle 1. As in FIG. 1, one can see the crown wheel 12 with the crown wheel shaft 13. On this crown wheel shaft 13 is disposed eccentrically a spherical head 19, over which the toothbrush shaft 15 reaches with a ring 20, molded to the shaft 15. This ring 20 is oriented such that its ring plane extends parallel to the longitudinal axis of the toothbrush shaft 15 owing to a connecting piece 21, running obliquely away from the toothbrush shaft 15 to the ring 20. Owing to the revolving movement of the spherical head 19, the toothbrush shaft 15 moves back and forth in the longitudinal direction, thus making the sliding movement mentioned earlier. At the same time it is swiveled back and forth about its longitudinal axis. Thus, in this embodiment the gear 14 represents simultaneously a sliding gear and a swivel gear for the toothbrush shaft 15.

Figure 3:
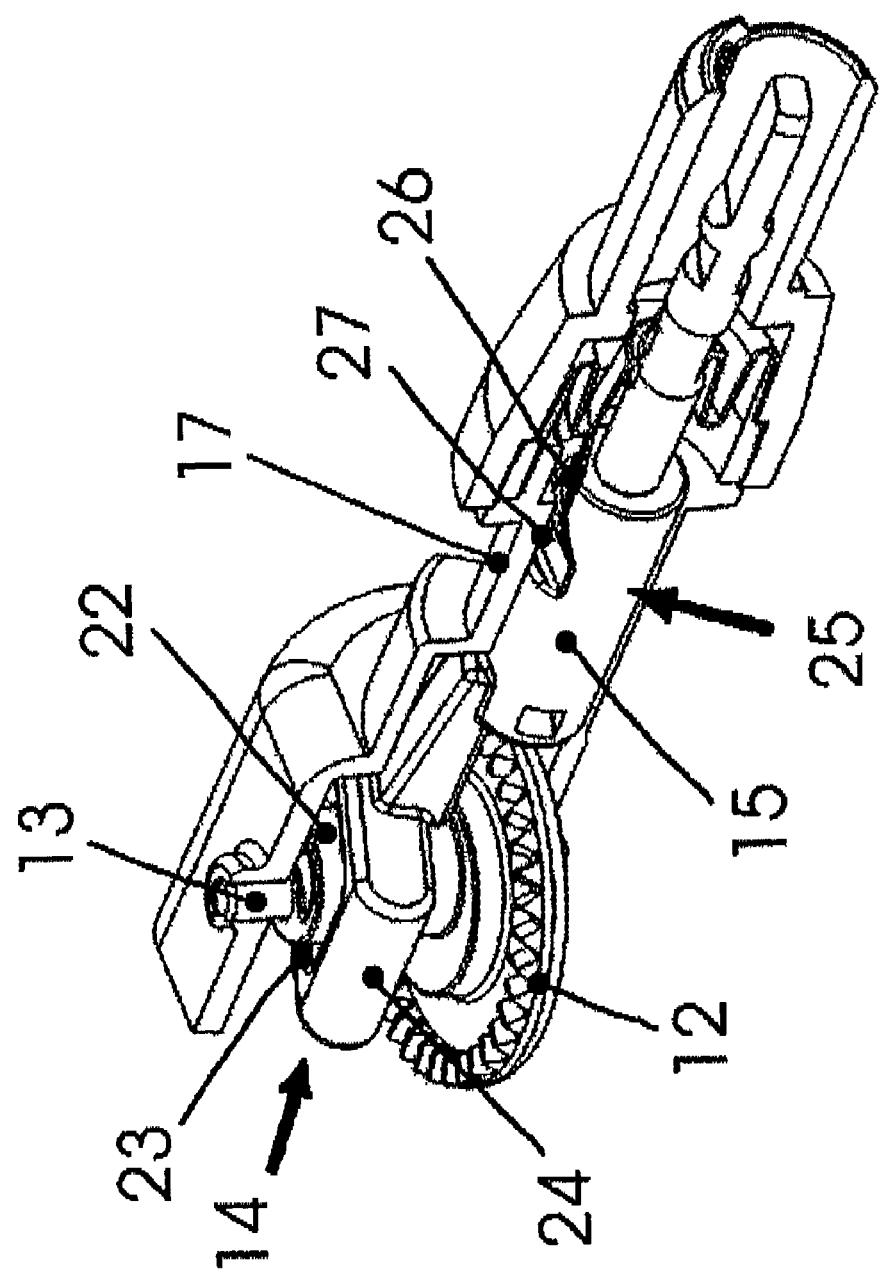
FIG. 3 is a perspective view, partly broken away for illustrative clarity, of a second embodiment of the gear area.

FIG. 3 depicts an embodiment of the gear 14 that is modified compared to that of FIG. 2. Thus, the crown wheel shaft 13 and the crown wheel 12 are connected non-rotatably to an eccentric 22, instead of a spherical head 19. The eccentric projects into a guide 23, which runs at right angles and belongs to a guide member 24 of the toothbrush shaft 15. The guide 23 has a width equivalent to the diameter of the eccentric 22, but in its transverse direction it is so long that the eccentric 22 does not rest in the transverse direction against the lateral limits of the guide 23. Thus, the revolving movement of the eccentric 22 brings about only a sliding movement of the toothbrush shaft 15. Thus, in this embodiment the gear 14 is only a sliding gear and not a combined sliding and swivel gear. In this embodiment a separate swivel gear 25, which can be formed by means of a twisted flattening 26 and a projection 27, which is oriented radially toward the inside and rests against the flattening and belongs to the housing 17, serves to produce the swivel movement of the toothbrush shaft.

Figure 4:
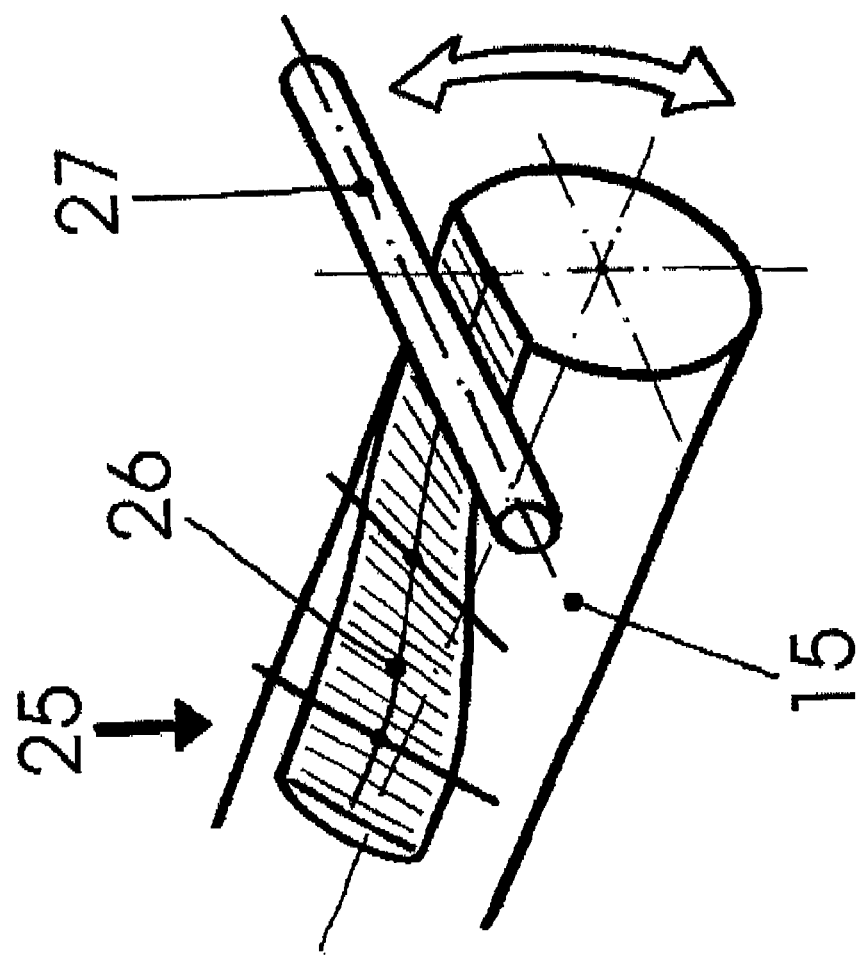
FIG. 4 is a perspective view, partly broken away for illustrative clarity, of a swivel gear for the toothbrush shaft.

The construction and the function of this swivel gear 25 can be seen the best in FIG. 4. Compared to FIG. 3, it significantly enlarges a sub-area of the toothbrush shaft 15 with the twisted flattening 26, against which the projection 27, designed as a pin in this example, rests. It shows that the toothbrush shaft 15 must rotate clockwise, if it is slid to the right, as shown in FIG. 4. Correspondingly, it must rotate counterclockwise if it is moved out of its right end position (not illustrated) back into the indicated left end position.

Figure 5:
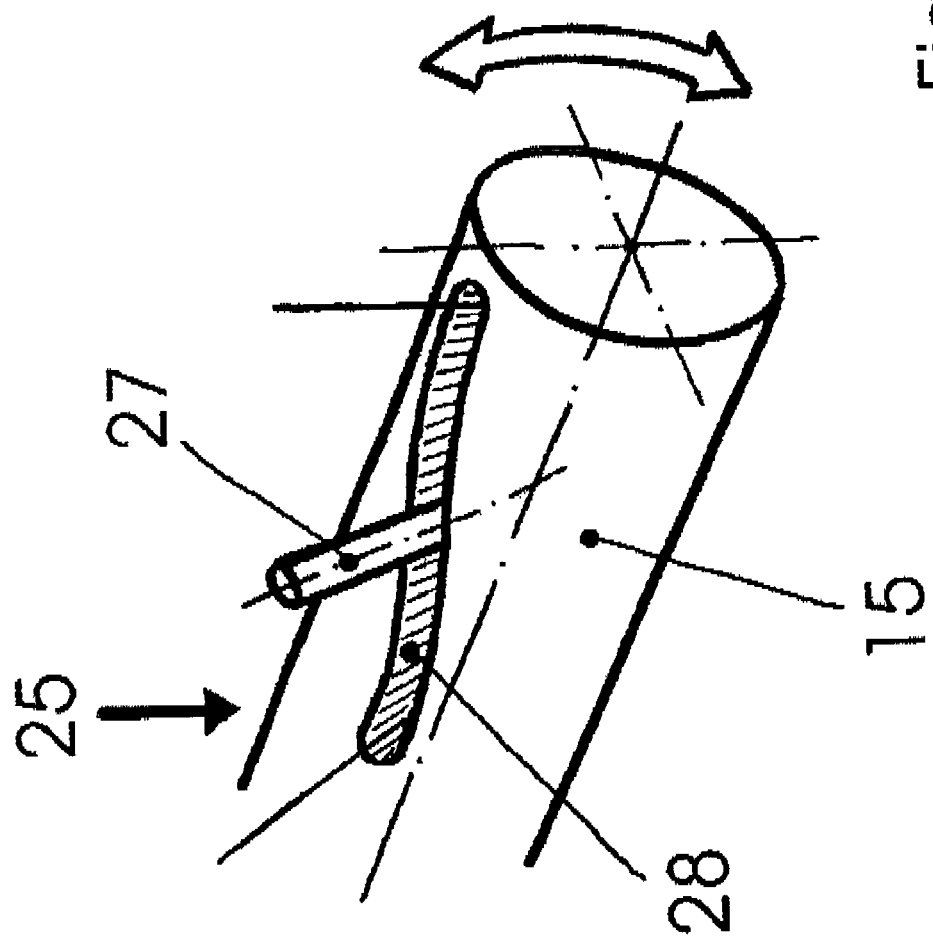
FIG. 5 is perspective view, partly broken away for illustrative clarity, of a second embodiment of a swivel gear for the toothbrush shaft.

The swivel gear, according to FIG. 5, has, instead of the flattening 26, an obliquely running groove 28, which leads radially into the toothbrush shaft 15, and into which the projection 27 projects radially. Correspondingly the reciprocating oscillatory movement of the toothbrush shaft 15 is realized automatically if the toothbrush shaft 15 slides to the right and the left, when it thus executes its sliding movement produced by the gear 14.

FIG. 6 shows that the swivel gear 25 can also be disposed in the brush head 3. In so doing, the front end 9 of the connecting rod 8 has an obliquely running groove 29, into which projects the bristle holder plate 4 with an arm 30, which is attached stationarily to the shaft. The bristle holder plate 4 is held swivelably in the brush head 3 by means of a swivel shaft 35, which runs offset parallel to the longitudinal axis of the connecting rod 8. In this embodiment the connecting rod 8 does not make any oscillatory movement about its longitudinal axis, but rather only a lifting movement in the direction of its longitudinal axis. The slanted groove 29 leads in connection with the arm 30 to the bristle holder plate 4 swiveling back and forth about the swivel shaft 35.

Figure 7:
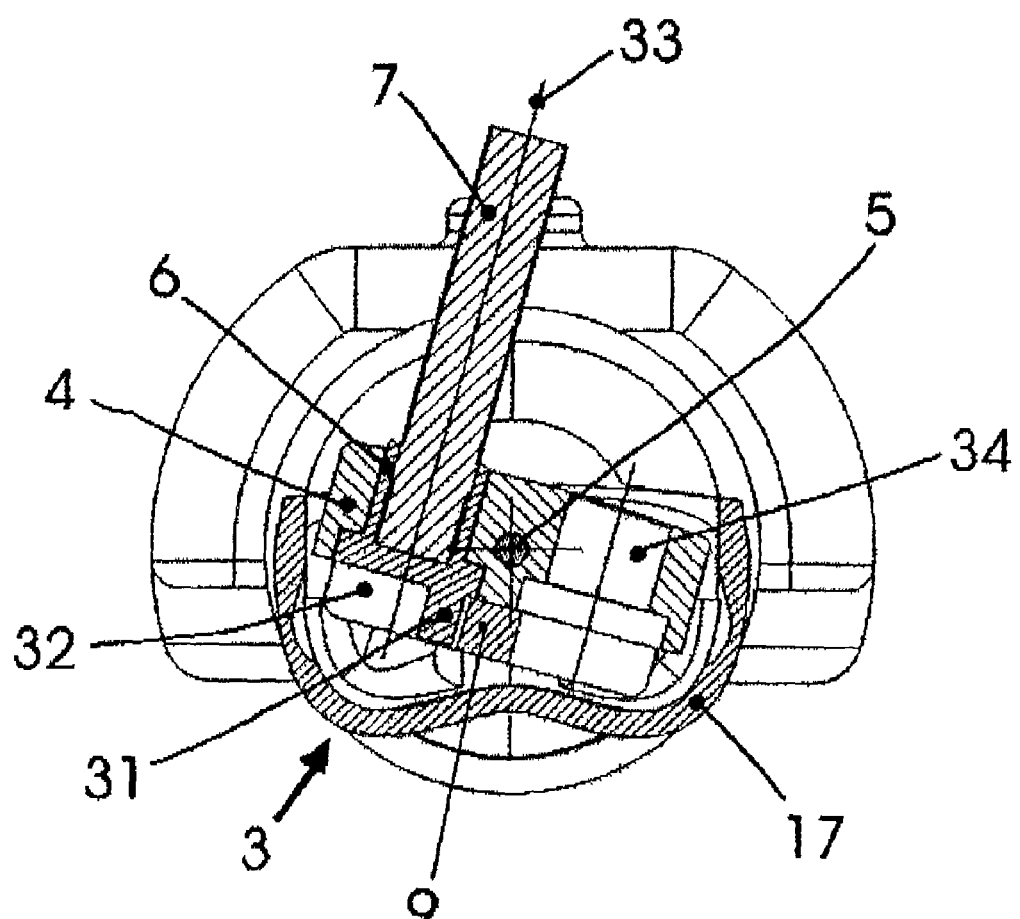
FIG. 7 is a transverse cross-sectional view of another embodiment of the toothbrush head.

FIG. 7 shows in detail how the brush head 3 can be designed in the embodiment according to FIGS. 1 to 5. The bristle holder plate 4 is mounted in turn in the housing 17 of the brush head 3 such that it oscillates about the shaft 5, running in the longitudinal direction. Furthermore, it shows how the tufts of bristles 7 are held in the bristle holder 6. The bristle holder 6 is inserted rotatably into the bristle holder plate 4 and has an eccentric pin 31, which projects into a transverse groove 32 of the front end 9 of the connecting rod 8. When the front end 9 executes its reciprocating sliding movement, which is oriented perpendicularly to the drawing plane in FIG. 7, then the bristle holder 6 swivels about an axis of rotation 33.

The right hand side of FIG. 7 shows only one borehole 34 in the bristle holder plate 4. A bristle holder 6 with tufts of bristles 7 must also be inserted into said borehole.

FIG. 8 serves to further illustrate the design of the toothbrush according to FIGS. 1, 3 and 7. One can see there the toothbrush shaft 15, which is set by the gear 14 in the handle 1 into the reciprocating sliding movement and the oscillatory rotating movement which is transferred from the toothbrush shaft 15 to the connecting rod 8 in the brush member 2. Furthermore, it is evident that the front end 9 of the connecting rod 8 has altogether three transverse grooves 32, 32' and 32", so that three tufts of bristles 7, 7' and 7" can be set into an oscillatory rotating movement. What was not illustrated was that three tufts of bristles 7 are also fixed rotatably on the right side of the toothbrush head 3.

This application claims the priority of German patent application No. 102 14 803.1, filed Apr. 4, 2002, the disclosure of which is expressly incorporated by reference herein.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An electric toothbrush comprising a handle and a brush member which comprises a brush head and a connecting rod capable of a sliding movement reciprocating in a longitudinal direction and an oscillatory movement about the longitudinal direction; wherein bristle holders are mounted rotatably in a bristle holder plate in the brush head, said bristle holders being set into an oscillatory rotating movement by the connecting rod; wherein the bristle holder plate is set into oscillatory movement about the longitudinal axis of the toothbrush by the connecting rod; wherein the bristle holder plate in the brush head is mounted so as to oscillate about a shaft running in the longitudinal direction of the toothbrush; and the brush member is connected non-rotatably to the handle.

2. An electric toothbrush as claimed in claim 1, wherein the oscillatory movement of the connecting rod about its longitudinal axis is caused by a gear disposed in the handle and which is formed by holding the connecting rod such that it rotates relative to the brush member about its longitudinal axis; and wherein the connecting rod rests with its front end so as to slide axially against the bristle holder plate.

3. An electric toothbrush as claimed in claim 2, wherein the front end of the connecting rod is bent at right angles and is oriented parallel to the longitudinal axis of the connecting rod.

4. An electric toothbrush as claimed in claim 2, wherein the gear in the handle is formed by an eccentric oriented at right angles to a longitudinally disposed toothbrush shaft linking the gear to the connecting rod and thus also at right angles to the connecting rod; and a guide member of the toothbrush shaft is formed with a guide which is oriented at right angles to the longitudinal axis of the toothbrush shaft and which reaches over the eccentric.

5. An electric toothbrush as claimed in claim 2, wherein the gear is formed exclusively for generating a sliding movement of the toothbrush shaft and, in addition to the gear, a swivel gear is provided for generating the swiveling movement of the toothbrush shaft.

6. An electric toothbrush as claimed in claim 5, wherein the swivel gear has a twisted flattening on the toothbrush shaft and a radial projection which is stationary in the housing and rests against said flattening.

7. An electric toothbrush as claimed in claim 6, wherein the swivel gear has a slanted groove which runs radially into the toothbrush shaft and into which projects a radial projection that is stationary in the housing.

8. An electric toothbrush as claimed in claim 5, wherein the swivel gear is disposed in the handle just like the gear for the sliding movement.

9. An electric toothbrush as claimed in claim 8, wherein the bristle holder plate in the toothbrush head is mounted swivelably on a swivel shaft which is oriented parallel to the longitudinal axis of the brush member on two opposing sides; and the connecting rod in the brush member is guided non-rotatably.

10. An electric toothbrush as claimed in claim 6, wherein the swivel gear is disposed in the brush head and has a groove which runs obliquely to the sliding direction of the connecting rod and into which projects an arm which is oriented radially to the swivel shaft of the bristle holder plate and is connected stationarily to the bristle holder plate.

11. An electric toothbrush as claimed in claim 5, wherein the gear has a spherical head designed as an eccentric, and the toothbrush shaft reaches with a ring offset radially to its longitudinal axis, over the spherical head.

12. An electric toothbrush as claimed in claim 1, wherein the shaft in the brush head is held on both sides of the bristle holder plate and projects with its free end into the connecting rod which is bent at right angles.

* * * * *